United States Patent [19]

Vasilenko et al.

[11] 4,317,360

[45] Mar. 2, 1982

[54] APPARATUS FOR DIFFERENTIAL THERMAL ANALYSIS

[76] Inventors: Vladimir I. Vasilenko, prospekt Vernadskogo, 87, kv. 38; Jury A. Krakovetsky-Kocherzhinsky, prospekt Vernadskogo, 69 "A", kv. 39; Evgeny A. Shishkin, ulitsa Klovsky pusk, 18, kv. 82; Jury A. Bojko, ulitsa Chkalova, 32, kv. 8, all of Kiev, U.S.S.R.

[21] Appl. No.: 159,849

[22] Filed: Jun. 16, 1980

[51] Int. Cl.³ .................................. G01K 17/04
[52] U.S. Cl. ........................................... 73/15 B
[58] Field of Search ........................ 73/15 B, 190 R

[56] References Cited

U.S. PATENT DOCUMENTS 3,336,790  8/1967  Nedumov ............................ 73/15
3,524,340  8/1970  Kocherzhinsky et al. ............ 73/15

OTHER PUBLICATIONS

Rupert, "Calibrated Derivative Thermal Analysis Apparatus for Detecting Phase Trasitions in High Temperature Materials", in Rev. Sci. Inst., vol. 45, No. 9, 9/74, pp. 1127-1133.

Primary Examiner—Herbert Goldstein
Attorney, Agent, or Firm—Lilling & Greenspan

[57] ABSTRACT

An apparatus comprises a block defining two chambers having openings in the bottom portions thereof. A crucible for a sample is installed in one of the block chambers, and in another chamber there is installed a crucible for a standard material. A baffle is positioned between the sample and the corresponding opening in the block. Between the standard material and the corresponding opening there is also positioned a baffle. Said baffles are made from a material similar to that of the block.

The apparatus further comprises two photoelectric pyrometers. The first photoelectric pyrometer is pointed through the corresponding opening at the baffle positioned between the sample and said opening. The second photoelectric pyrometer is pointed through the corresponding opening at the baffle positioned between the standard material and said opening. Recording instruments are electrically connected to the outputs of the photoelectric pyrometers.

5 Claims, 3 Drawing Figures

APPARATUS FOR DIFFERENTIAL THERMAL ANALYSIS

BACKGROUND OF THE INVENTION

1. Field of the Invention

The present invention relates to the design of equipment intended for investigating material properties, namely to the apparatus for differential thermal analysis. The invention may prove most advantageous under laboratory conditions for investigating phase transformations in refractory materials.

Though the principle of differential thermal analysis has been known for a comparatively long time and has found wide application in investigating various materials, the problem of increasing accuracy and reliability of results is urgent up to now. In addition, maximum operating temperature of the majority of manufactured devices intended for thermal analysis does not exceed 1800° C. This feature considerably limits measuring capability of such devices due to the absence of the possibility of investigating phase transformations in numerous refractory materials.

2. Description of the Prior Art

Known in the art is an apparatus for differential thermal analysis allowing materials to be investigated at temperatures of up to 2300° C. (see U.S. Pat. No. 3,524,340; British Patent Specification No. 1,133,396; German Pat. No. 1,598,651; French Pat. No. 1,540,445). This apparatus comprises a heated block constructed from a refractory material and defining two chambers. In one of the block chambers there is mounted a crucible for a sample of the material being investigated and in another chamber there is mounted a crucible for a standard material. Hot junctions of a differential thermocouple are brought into contact with bottom portions of the crucibles. Recording instruments such as millivoltmeters and recorders are connected to said thermocouple.

The apparatus above described makes it possible to carry out differential thermal analysis at temperatures of up to 2300° C. Such a temperature limit is dependent on the properties of the thermocouple material. When heating the sample in an electric furnace, some babbles occur in the thermocouple, thus complicating the recording of the parameters being measured.

There is also known in the art an apparatus for differential thermal analysis at higher temperatures (see H. D. Heetderks, E. Rudy, T. Eckert, Planseeberichte für Pulvermetallurgie, 1965,13,2,105). This apparatus comprises a block constructed from a refractory material and defining two chambers having openings. The openings are provided in covers of the block chambers.

Bottom portions of the chambers are made one-piece and have no openings. In one chamber there is installed a crucible for a sample. In another chamber there is installed a crucible for a standard material. A photoelectric pyrometer is pointed through one opening directly at the sample. Through another opening there is also pointed a photoelectric pyrometer at the standard material. Recording instruments are electrically connected to the outputs of the photoelectric pyrometers.

An obvious advantage of such apparatus consists in the removal of a sensing element from the high temperature zone so as to allow the range of the working temperatures to be significantly expanded. To eliminate the dependence of signals of the photoelectric pyrometers upon the degree of blackness of the object being investigated, blind openings simulating an absolutely black body are provided in the sample and in the standard.

Each photoelectric pyrometer is pointed at the bottom of the corresponding opening in the sample and in the standard. The necessity for simulating an absolutely black body causes some difficulties when using the above described apparatus. It is known that a cylindrical blind opening corresponds to a model of an absolutely black body only when the ratio between the depth and the diameter of said opening is not less than 7. But with such relative dimensions of the openings, the sizes of the sample and of the standard must be sufficiently large while the weight thereof should not be less than 15 g. When investigating alloys based on rare and precious metals, this consideration exerts a considerable influence upon the experimental cost. When investigating hard and brittle materials, the provision of openings in the sample and in the standard entails great processing difficulties. Products of the material evaporation, transferred by convective flows of an inert gas being the medium for heating the block, contribute a significant error to the analysis results. Measuring capability of the apparatus is constricted by the fact that the model of the black body gets damaged during the process of melting the sample. This fact eliminates the possibility of determining the end melting temperature of the sample material and recording temperatures of some phase transformations in the melt, e.g. during the solidification thereof.

SUMMARY OF THE INVENTION

The main object of the present invention is to provide an apparatus for differential thermal analysis ensuring elimination of the dependence of the signals of photoelectric pyrometers upon the degree of blackness of the object being investigated without simulating an absolutely black body.

Another object of the invention is to expand measuring capability of the apparatus for differential thermal analysis at high temperatures.

A further object of the invention is to provide an apparatus having photoelectric pyrometers, which apparatus makes it possible to investigate materials during the process of melting thereof.

An additional object of the invention is to reduce the sample dimensions and to lower the experiment cost.

A further object of the invention is to lower the power consumption required for heating the sample and the standard.

Another important object of the invention is to reduce the error when determining the temperature of phase transformations.

These and other objects of the invention are attained by an apparatus for differential thermal analysis comprising a block defining two chambers having openings; a crucible for a sample and a crucible for a standard material, both placed in the chambers of said block; photoelectric pyrometers of which one is pointed at the opening of the chamber containing the crucible for a sample and the other of which is pointed at the opening of the chamber containing the crucible for a standard material; and recording instruments electrically connected to the outputs of said photoelectric pyrometers. According to the invention, said openings are provided in bottom portions of said block chambers, the photoelectric pyrometers are pointed at baffles positioned between said openings and correspondingly between the sample and the standard material, and said baffles are made from a material similar to that of the block. Temperatures of the baffles are defined by the temperatures of the sample and of the standard. In this case, it is possible to calibrate a temperature scale of the recording instruments in accordance with the critical temperatures of well-known materials. This allows the possible difference between the temperature of the baffle and that of the sample to be automatically taken into account. Thus, the above design features (orientation of the photoelectric pyrometers in respect to the baffles) eliminate the need for simulating an absolutely black body and, hence, a possibility is provided for investigating comparatively small samples having a weight of 1 to 2 g. Such a procedure results in a considerable decrease in power consumption and in the experimental cost.

The materials of the block and of the baffles being similar, an inevitable spraying the block material into the baffles does not result in changes in the surface composition of the latter and practically does not exert influence upon the degree of blackness thereof. Measurement accuracy is favoured by the fact that the pyrometers are orientated to the baffles rather than to the material being investigated as in the prior art apparatus. Products of the material evaporation exert significantly lower inluence upon the light flow sensed by the photoelectric pyrometers. The apparatus makes it possible to investigate materials being both in solid and in melted states.

Structurally, the simpliest is such a modification of the apparatus wherein the bottom portions of the crucibles serve as the baffles. In this case, the crucibles must be made from a material similar to that of the block.

More preferred is a modification of the apparatus wherein the baffles are constructed in the form of plates mounted beneath the bottom portions of the crucibles and are in contact therewith. The block may be made one material, e.g. metal, while the crucibles are made from some other materials, e.g. from ceramics.

To prevent the plate buckling, it is expedient that said plate be convex and that the bottom portion of the corresponding crucible be supported by the top portion of the convex surface thereof.

From the economical point of view, it is advisable that both the block and the plates be made from tungsten.

BRIEF DESCRIPTION OF DRAWINGS

Now the invention will be described by way of specific examples thereof with reference to the accompanying drawings wherein.

DETAILED DESCRIPTION OF THE INVENTION

Figure 1:
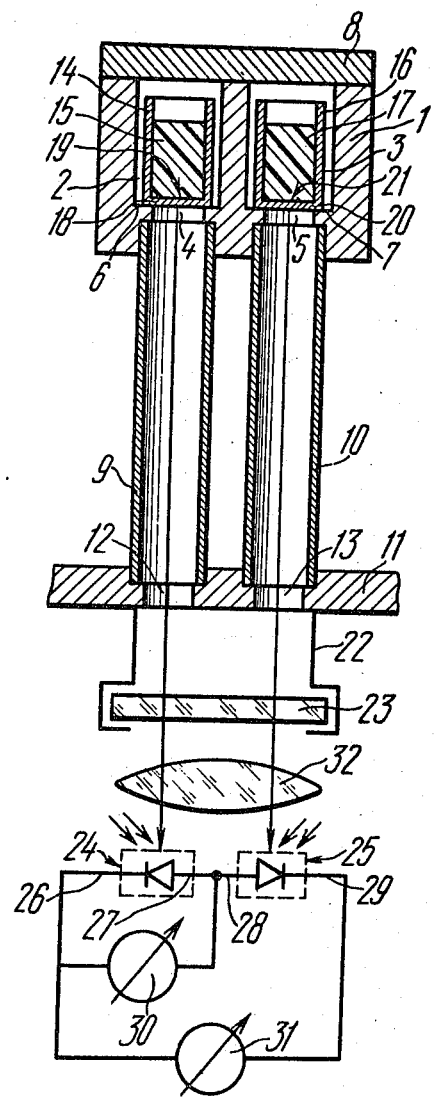
FIG. 1 is a front view of the apparatus for differential thermal analysis, according to the invention.

An apparatus for differential thermal analysis comprises a block 1 (FIG. 1) defining two chambers 2 and 3 having openings 4 and 5. The opening 4 is provided in a bottom portion 6 of the chamber 2 and the opening 5 is provided in a bottom portion 7 of the chamber 3. The chambers 2 and 3 of the block 1 are closed from above with a cover 8. The block 1 is positioned on tubular stands 9 and 10 supported by an upper surface of a base 11. The tubular stand 9 has an upper end mounted into a lower portion of the block 1 coaxially with the opening 4 of the chamber 2 and the tubular stand 10 has an upper end mounted into a lower portion of the block 1 coaxially with the opening 5 of the chamber 3. Beneath the lower ends of the tubular stands 9 and 10 in the base 11 there are respectively provided through openings 12 and 13. The opening 12 is made coaxial to the tubular stand 9 and the opening 13 is made coaxial to the tubular stand 10.

In the chamber 2 of the block 1 there is mounted a crucible 14 for a sample 15 and in the chamber 3 there is mounted a crucible 16 for a standard material 17. A bottom portion 18 of the crucible 14, according to the invention, serves as a baffle 19 positioned between the sample 15 and the opening 4 of the chamber 2. A bottom portion 20 of the crucible 16, according to the invention, serves as a baffle 21 positioned between the standard material 17 and the opening 5 of the chamber 3. The baffles 19 and 21, according to the invention, are made from a material similar to that of the block 1.

A branch pipe 22 having an opening 23 positioned at the lower end thereof is fixed to the lower surface of the base 11 beneath the openings 12 and 13.

The apparatus further comprises two photoelectric pyrometers 24 and 25 positioned beneath the opening 23. The photoelectric pyrometers may be variously constructed, but in the given case it is expedient to apply a photoelectric pyrometer with a photodiode serving as a sensing element.

The photoelectric pyrometer 24 is pointed, according to the invention, through the opening 12 of the base 11, the tubular stand 9 and the opening 4 of the chamber 2, at the baffle 19 positioned between the sample 15 and the opening 4.

The photoelectric pyrometer 25 is pointed, according to the invention, through the opening 13 of the base 11, the tubular stand 10 and the opening 5 of the chamber 3, at the baffle 21 positioned between the standard material 17 and the opening 5.

The photoelectric pyrometer 24 is provided with two outputs 26 and 27 and the photoelectric pyrometer 25 is provided with outputs 28 and 29. Recording instruments 30 and 31 are electrically connected to the outputs of said photoelectric pyrometers 24 and 25.

Millivoltmeters or potentiometer-type recorders may be used as the recording instruments 30 and 31. The recording instrument 30 is connected to the outputs 26 and 27 of the photoelectric pyrometer 24 and serves for measuring the temperature of the sample 15.

The recording instrument 31 is connected to the output 26 of the photoelectric pyrometer 24 and to the output 29 of the photoelectric pyrometer 25 in the comparison circuit, and serves for measuring the difference between temperatures of the sample 15 and the standard material 17.

The photoelectric pyrometers 24 and 25 are with their outputs 27 and 28, respectively, in a series-opposed connection.

A lens 32 is positioned between the photoelectric pyrometers 24 and 25 and the opening 23.

Figure 2:
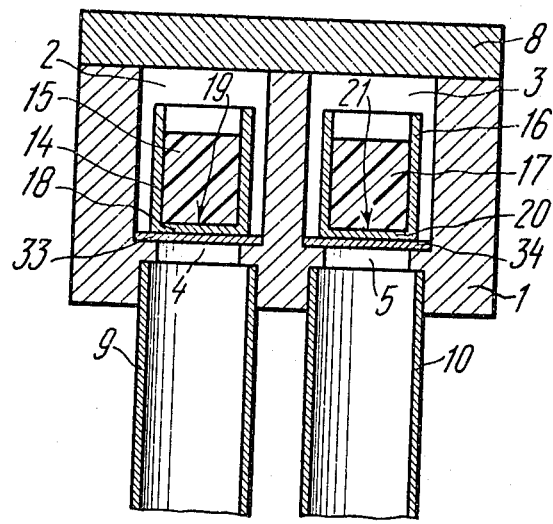
FIG. 2 is an elevational view of a modification of the apparatus of the present invention, provided with baffles in the form of plates.

FIG. 2 shows a modification of the block 1 of the inventive apparatus wherein the baffles 19 and 21 are made, according to the invention, in the form of plates 33 and 34, respectively. The flat plate 33, according to the invention, is mounted beneath the bottom portion 18 of the crucible 14 and is in contact therewith, and the flat plate 34 is mounted beneath the bottom portion 20 of the crucible 16 and is in contact therewith. The plates 33 and 34 are made from a material similar to that of the block 1. In accordance with the invention, the block 1 and the plates 33 and 34 should preferably be made from tungsten.

Figure 3:
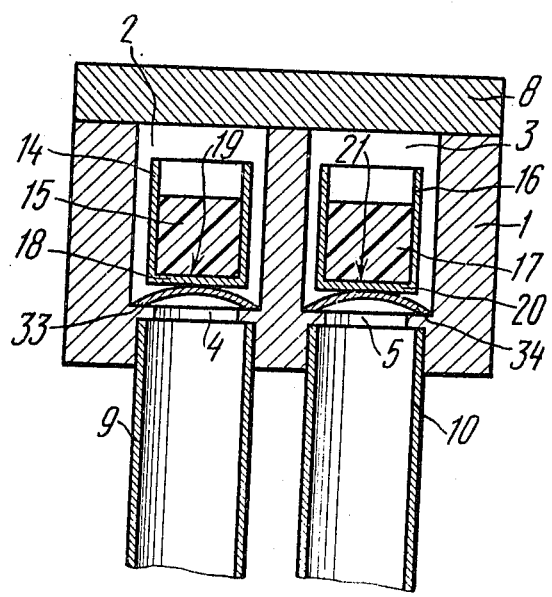
FIG. 3 is an elevational view of a modification of the apparatus of the present invention, provided with convex plates.

FIG. 3 shows a modification of the block 1 of the inventive apparatus, provided with convex plates 33 and 34.

According to the invention, the convex plate 33 is positioned beneath the bottom portion 18 of the crucible 14, said bottom portion 18 being supported by the top of the convex surface of the plate 33. The convex plate 34 is positioned beneath the bottom portion 20 of the crucible 16, said bottom portion 20 being supported by the top of the convex surface of the plate 34.

The apparatus above described operates as follows. With the cover 8 being open, the sample 15 of the material being investigated is placed into the crucible 12 while the standard material 17 is placed into the crucible 16. Then the cover 8 is closed, and the block 1 is heated. A material, which is not subject to any phase transformations during the process of heating within the investigated temperature range, is used as a standard. When heating the block 1, the crucibles 14 and 16, containing the sample 15 and the standard material 17, are also heated. The baffles 19 and 21 (the bottom portions 18 and 20 of the crucibles 14 and 16 in FIG. 1) are also heated, their temperature being substantially defined by the temperatures of the sample 15 and of the standard material 17, respectively. The light radiation flow emitted by the baffle plate 19 is sensed by the photoelectric pyrometer 24 and the radiation emitted by the baffle 21 is sensed by the photoelectric pyrometer 25.

The recording instrument 30, being properly calibrated, indicates the temperature of the sample 15 and the recording instrument 31 indicates the difference between the temperature of the sample 15 and that of the standard material 17. When using recorders (not shown) as the recording instruments 30 and 31, a graphic display of the temperature variation of the sample 15 and of the temperature difference between the sample 15 and the standard material 17 is obtained. During the process of phase transformations occuring in the material being investigated (the sample 15), the temperature difference between the sample and the standard changes to a considerable degree.

Critical temperature points of the material being investigated are determined by recording the initial and end temperatures of the phase transformations both in the solid state and in the process of melting the material.

Modifications of the apparatus shown in FIGS. 2 and 3 operate substantially as described above. However, the plates 33 and 34 serve as radiation sources for the measured light flows. The temperatures of the plates 33 and 34 vary similar to the temperatures of the sample 15 and of the standard 17 due to the intensive heat exchange between the crucibles 14 and 16 and said plates.

It will be understood that while the invention has been described herein in terms of specific embodiments, numerous modifications may be made in the invention without departing from the spirit and scope thereof as set forth in the appended claims.

What is claimed is:

1. An apparatus for differential thermal analysis, comprising:
    a block defining two chambers having openings in the bottom portions thereof;
    a crucible for a sample mounted on one of the chambers of said block;
    a crucible for a standard material mounted in another chamber of said block;
    a baffle positioned between the sample and the corresponding opening in said block, and made from a material similar to that of said block;
    a baffle positioned between the standard material and the corresponding opening in said block, and made from a material similar to that of said block;
    a first photoelectric pyrometer pointed through the corresponding opening at said baffle positioned between the sample and said opening in said block;
    a second photoelectric pyrometer pointed through the corresponding opening at said baffle positioned between the standard material and said opening in said block;
    recording instruments electrically connected to the outputs of said photoelectric pyrometers.

2. An apparatus as set forth in claim 1, wherein said bottom portions of said crucibles serve as said baffles, said crucibles being made from a material similar to that of said block.

3. An apparatus as set forth in claim 1, wherein said baffles are made in the form of plates mounted beneath said bottom portions of said crucibles and are in contact therewith.

4. An apparatus as set forth in claim 3, wherein each plate is convex, and said bottom portion of the corresponding crucible is supported by the top of the convex surface thereof.

5. An apparatus as set forth in claim 4, wherein said plates and said block are made from tungsten.

* * * * *